United States Patent
Groth et al.

(10) Patent No.: US 10,679,350 B2
(45) Date of Patent: Jun. 9, 2020

(54) METHOD AND APPARATUS FOR ADJUSTING A MODEL OF AN ANATOMICAL STRUCTURE

(71) Applicant: KONINKLIJKE PHILIPS N.V., Eindhoven (NL)

(72) Inventors: Alexandra Groth, Hamburg (DE); Rolf Jürgen Weese, Norderstedt (DE); Heike Carolus, Hamburg (DE); Jochen Peters, Norderstedt (DE)

(73) Assignee: KONINKLIJKE PHILIPS N.V, Eindhoven (NL)

( * ) Notice: Subject to any disclaimer, the term of this patent is extended or adjusted under 35 U.S.C. 154(b) by 104 days.

(21) Appl. No.: 16/100,404

(22) Filed: Aug. 10, 2018

(65) Prior Publication Data
US 2020/0051247 A1    Feb. 13, 2020

(51) Int. Cl.
*G06T 7/10*    (2017.01)
*G06T 15/08*    (2011.01)
(Continued)

(52) U.S. Cl.
CPC .............. *G06T 7/10* (2017.01); *G06T 7/0012* (2013.01); *G06T 15/08* (2013.01); *G06T 15/205* (2013.01); *A61B 2034/105* (2016.02); *G06T 17/205* (2013.01); *G06T 2200/24* (2013.01); *G06T 2210/41* (2013.01); *G06T 2219/028* (2013.01); *G06T 2219/2021* (2013.01); *G16H 30/20* (2018.01)

(58) Field of Classification Search
CPC .............. A61B 2034/105; G16H 30/20; G06T 7/0012; G06T 7/10; G06T 15/08; G06T 15/205; G06T 17/205; G06T 2200/24; G06T 2210/41; G06T 2219/028; G06T 2219/2021
See application file for complete search history.

(56) References Cited

U.S. PATENT DOCUMENTS

| 7,689,021 B2 | 3/2010 | Shekhar et al. |
| 9,014,466 B2 | 4/2015 | Kaus et al. |

(Continued)

FOREIGN PATENT DOCUMENTS

| WO | 2012017375 A2 | 2/2012 |
| WO | 2017001476 A1 | 1/2017 |

OTHER PUBLICATIONS

Kretschmer et al. "Interactive patient-specific vascular modeling with sweep surfaces." IEEE transactions on visualization and computer graphics 19.12 (2013): 2828-2837. (Year: 2013).*

(Continued)

*Primary Examiner* — Katrina R Fujita

(57) ABSTRACT

There is provided a method and apparatus for adjusting a model of an anatomical structure in a sequence of images of the anatomical structure. The model is placed with respect to the anatomical structure in the sequence of images. A user input is received to adjust the model in a selected image of the sequence, and based on the user input, a part of the model that lies in the selected image and a previously unadjusted part of the model that lies in one or more other images of the sequence is adjusted, whilst fixing in place a previously adjusted part of the model that lies in other images of the sequence.

15 Claims, 3 Drawing Sheets

(51) Int. Cl.
  *G06T 7/00* (2017.01)
  *G06T 15/20* (2011.01)
  *A61B 34/10* (2016.01)
  *G06T 17/20* (2006.01)
  *G16H 30/20* (2018.01)

(56) References Cited

U.S. PATENT DOCUMENTS

| | | | |
|---|---|---|---|
| 2009/0310835 A1* | 12/2009 | Kaus | G06T 17/20 |
| | | | 382/128 |
| 2010/0195887 A1 | 8/2010 | Abe et al. | |
| 2013/0002646 A1 | 1/2013 | Lin et al. | |
| 2014/0249790 A1* | 9/2014 | Spilker | G16H 30/20 |
| | | | 703/11 |
| 2015/0104090 A1* | 4/2015 | Hopfgartner | G06T 17/10 |
| | | | 382/131 |
| 2019/0183579 A1* | 6/2019 | Kosior | A61B 6/504 |

OTHER PUBLICATIONS

Heckel, et al., "3D contour based local manual correction of tumor segmentations in CT scans", Medical Imaging 2009: Proc. of SPIE, vol. 7529, pp. 72593L-1 to 72593L-9.

Heckel, et al., "Sketch-Based Editing Tools for Tumour Segmentation in 3D Medical Images", Computer Graphics Forum, vol. 32 (2013), No. 8, pp. 144-157.

Sun, S., "Automated and interactive approaches for optimal surface finding based segmentation of medical image data", University of Iowa, Iowa Research Online, Theses and Dissertations, Dec. 2012, available at http://ir.uiowa.edu/etd/3543, 215 pages.

* cited by examiner

METHOD AND APPARATUS FOR ADJUSTING A MODEL OF AN ANATOMICAL STRUCTURE

TECHNICAL FIELD OF THE INVENTION

This disclosure relates to the field of image processing and, in particular, to a method and apparatus for adjusting a model of an anatomical structure in a sequence of images of the anatomical structure.

BACKGROUND OF THE INVENTION

Medical image processing often uses segmentation to determine the location of features of interest in a medical image and to generate a patient-specific model of the anatomical structure in the image. This patient-specific model can then be used to make measurements of the anatomical structure (for example, to measure the left ventricular volume over the heart cycle), for diagnosis, treatment planning (for example, in aortic valve implant fitting), or for the prediction of disease (for example, biophysical models). In order to extract the shape of an anatomical structure from medical images, different methods of segmentation can be used, such as, for example, a model-based segmentation framework in which an adjustable model of the anatomical structure is placed in the image to segment the anatomical structure.

An example of such a model-based segmentation framework is provided in an article by Ecabert et al., entitled "*Segmentation of the heart and great vessels in CT images using a model-based adaptation framework, Medical Image Analysis*", Volume 15, Issue 6, December 2011, Pages 863-876, which describes detailed local correction and manual editing of a multi-color mask overlain on an image of a heart.

However, in these existing techniques, if the segmentation of an anatomical structure in an image is inaccurate (for example, if the segmentation results in a model that does not accurately reflect the shape of the anatomical structure in the image), various correction mechanisms are available whereby a physician can manually adjust the model to correct the segmentation result. For example, a physician may manually adjust the model by dragging points of the model towards the correct features of the anatomical structure in the image. For the purposes of efficiency, existing correction methods typically modify the model in multiple images simultaneously as this reduces the manual work involved and can keep the segmentation consistent across the images. For example, a modification may be propagated through multiple images in time-series of two-dimensional images, or through multiple images in time-series of three-dimensional images and/or in all three-dimensions in the case of three-dimensional images.

As a result, not only parts of the model belonging to a currently displayed image are modified, but also parts of the model belonging to neighboring images in the sequence are modified. This means that, following an adjustment to the model in an image, the physician must review neighboring images to ensure that any changes that were propagated through to the neighboring images are reasonable. In some instances, for example, the physician will need to review images that have already been previously inspected to determine whether any modifications that have propagated to those previously inspected images have resulted in errors that require the model to be re-adjusted in those images. In order to ensure that no errors result from a modification to the model in one image, the physician would need to check the model in all other images.

In the case of adjusting a model in a four-dimensional image comprising a time-sequence of three-dimensional images, the propagation of adjustments to the model across the time-sequence of three-dimensional images can occur in both space (for example, to images at different points in space, such as neighboring images) and time (for example, to images at different points in time). In such examples, it becomes even more complicated and time consuming to review adjustments to the model as the adjustments may have been propagated in both space and time.

Thus, the process for adjusting a model of an anatomical structure becomes inefficient once again and is also complex. There is thus a need for an improved method and apparatus for adjusting a model of an anatomical structure in a sequence of images of the anatomical structure.

SUMMARY OF THE INVENTION

As noted above, a limitation with existing techniques for adjusting a model of an anatomical structure in a sequence of images of the anatomical structure is that the techniques result in errors that can propagate through multiple images in the sequence and the techniques are also inefficient and overly complex. It would thus be valuable to have an improved method for adjusting a model of an anatomical structure, which overcomes the problems described above.

Therefore, according to a first aspect of the invention, there is provided a method for adjusting a model of an anatomical structure in a sequence of images of the anatomical structure, the method comprising: placing the model with respect to the anatomical structure in the sequence of images; receiving a user input to adjust the model in a selected image of the sequence; and adjusting, based on the user input, a part of the model that lies in the selected image and a previously unadjusted part of the model that lies in one or more other images of the sequence, whilst fixing in place a previously adjusted part of the model that lies in other images of the sequence.

In some embodiments, the previously unadjusted part of the model lies in one or more images that are subsequent to the selected image in the sequence and the previously adjusted part of the model lies in images that precede the selected image in the sequence.

In some embodiments, the method further comprises fixing in place the adjusted part of the model that lies in the selected image for subsequent adjustments.

In some embodiments, adjusting a previously unadjusted part of the model that lies in the one or more other images of the sequence comprises using an interpolation to adjust the previously unadjusted part of the model that lies in the one or more other images of the sequence, based on the adjustment to the part of the model that lies in the selected image.

In some embodiments, the method further comprises receiving at least one further user input to adjust the model in at least one further image in the sequence; and adjusting, based on the at least one further user input, a part of the model that lies in the at least one further image, whilst fixing in place a previously adjusted part of the model that lies in other images of the sequence.

In some embodiments, the one or more other images of the sequence in which a previously unadjusted part of the model is adjusted are selected based on a property of the anatomical structure.

In some embodiments, the one or more other images of the sequence in which a previously unadjusted part of the model is adjusted lie within a predetermined radius of the selected image.

In some embodiments, the sequence of images comprises a time sequence of two-dimensional images, wherein each two-dimensional image in the sequence shows the anatomical structure at a subsequent point in time from the preceding two-dimensional image in the sequence.

In some embodiments, the sequence of images comprises a sequence of two-dimensional slices through a three-dimensional image, wherein each slice of the three-dimensional image in the sequence shows the anatomical structure at a subsequent two-dimensional spatial plane from the preceding slice of the three-dimensional image in the sequence.

In some embodiments, the sequence of images comprises a time sequence of three-dimensional images, wherein each three-dimensional image in the sequence shows the anatomical structure at a subsequent point in time from the preceding three-dimensional image in the sequence.

In some embodiments, the model of the anatomical structure comprises a mesh comprising a plurality of segments and the method further comprises determining which of the plurality of segments lie in the selected image in the sequence; and adjusting, based on the user input, one or more of the segments that are determined to lie in the selected image in the sequence.

In some embodiments, the one or more adjusted segments lying in the selected image comprise at least one segment of the mesh to which the received user input relates and one or more adjacent segments.

According to a second aspect of the invention, there is provided a computer program product comprising a computer readable medium, the computer readable medium having computer readable code embodied therein, the computer readable code being configured such that, on execution by a suitable computer or processor, the computer or processor is caused to perform the method described above.

According to a third aspect of the invention, there is an apparatus for adjusting a model of an anatomical structure in a sequence of images of the anatomical structure, the apparatus comprising: a processor configured to: place the model with respect to the anatomical structure in the sequence of images; receive a user input to adjust the model in a selected image of the sequence; and adjust, based on the user input, a part of the model that lies in the selected image and a previously unadjusted part of the model that lies in one or more other images of the sequence, whilst fixing in place a previously adjusted part of the model that lies in other images of the sequence.

In some embodiments, the processor is configured to control a user interface to render the adjusted model of the anatomical structure; and/or control a memory to store the adjusted model of the anatomical structure.

According to the aspects and embodiments described above, the limitations of existing techniques are addressed. In particular, according to the above-described aspects and embodiments, a model of an anatomical structure in a sequence of images of the anatomical structure can be adjusted in a simple and efficient manner, while errors propagating through multiple images are avoided to produce more reliable adjusted models of anatomical structures.

There is thus provided an improved method of adjusting a model of an anatomical structure in a sequence of images of the anatomical structure, which overcomes the existing problems.

BRIEF DESCRIPTION OF THE DRAWINGS

For a better understanding of the embodiments, and to show more clearly how they may be carried into effect, reference will now be made, by way of example only, to the accompanying drawings, in which.

DETAILED DESCRIPTION OF THE EMBODIMENTS

Figure 1:
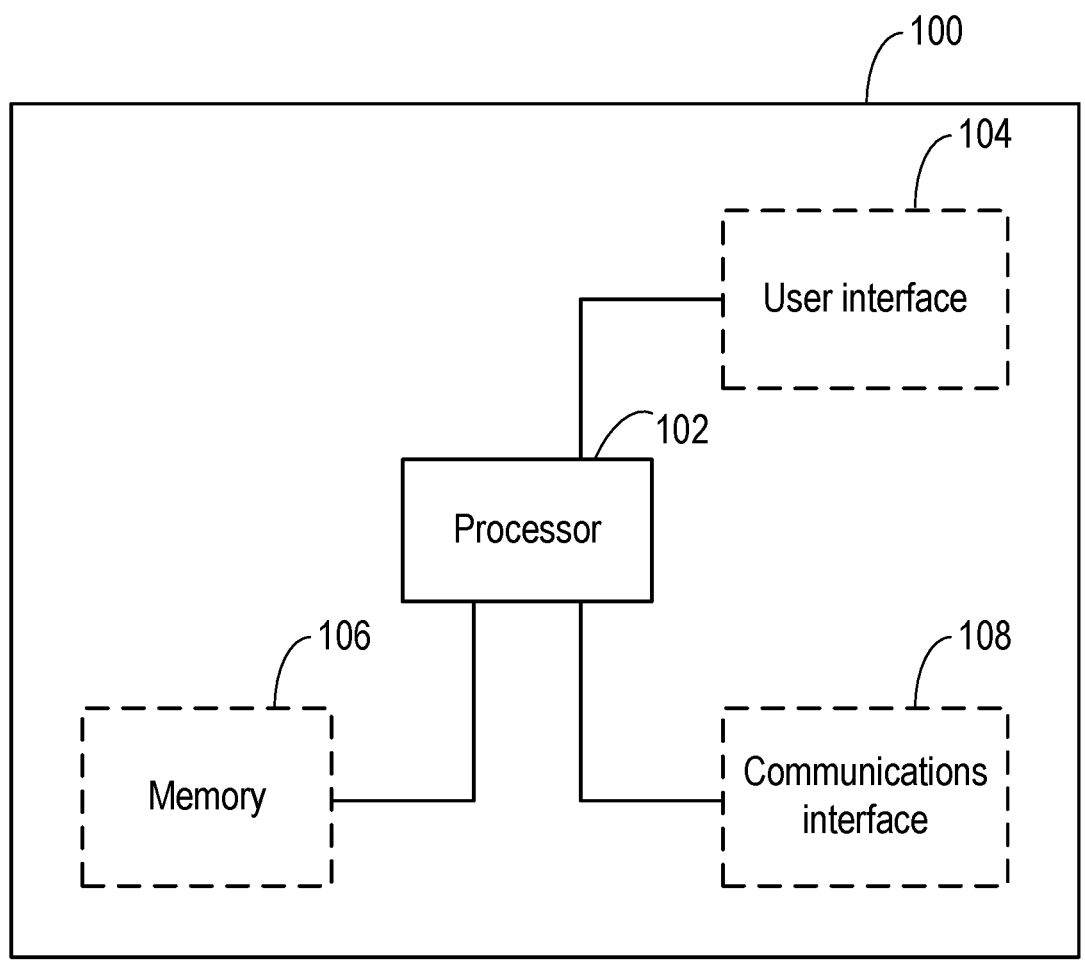
FIG. 1 is a block diagram of an apparatus for adjusting a model of an anatomical structure according to an embodiment.

FIG. 1 shows a block diagram of an apparatus 100 according to an embodiment that can be used for adjusting a model of an anatomical structure in a sequence of images of the anatomical structure.

With reference to FIG. 1, the apparatus 100 comprises a processor 102 that controls the operation of the apparatus 100 and that can implement the method described herein. The processor 102 can comprise one or more processors, processing units, multi-core processors or modules that are configured or programmed to control the apparatus 100 in the manner described herein. In particular implementations, the processor 102 can comprise a plurality of software and/or hardware modules that are each configured to perform, or are for performing, individual or multiple steps of the method according to the embodiments described herein.

Briefly, the processor 102 is configured to place the model of the anatomical structure with respect to the anatomical structure in the sequence of images, receive a user input to adjust (or modify) the model in a selected image of the sequence, and adjust (or modify), based on the user input, a part (or portion) of the model that lies in the selected image and a previously unadjusted part (or portion) of the model that lies in one or more other images of the sequence, whilst fixing in place a previously adjusted part (or portion) of the model that lies in other images of the sequence.

In this way, any parts of the model that have been previously adjusted by the user are fixed (or frozen) in place. This eliminates the need for the user to have to repeatedly check and re-adjust sections of the model that have already been adjusted and approved by the user.

In some embodiments, the apparatus 100 may also comprise at least one user interface 104. Alternatively or in addition, at least one user interface 104 may be external to (i.e. separate to or remote from) the apparatus 100. For example, at least one user interface 104 may be part of another device.

A user interface 104 may be for use in providing a user of the apparatus 100 (for example, a healthcare practitioner, a healthcare specialist, a care giver, a subject, or any other user) with information resulting from the method according to embodiments herein. The processor 102 may be configured to control one or more user interfaces 104 to provide information resulting from the method according to embodiments herein. For example, the processor 102 may be configured to control one or more user interfaces 104 to render (or output or display) one or more of the images in the sequence of images and/or the adjusted model of the anatomical structure. Alternatively or in addition, a user interface 104 may be configured to receive a user input. In other words, a user interface 104 may allow a user of the apparatus 100 to manually enter instructions, data, or information. For example, in some embodiments, the user interface 104 may allow the user of the apparatus 100 to provide a user input to adjust the model of the anatomical structure in the manner described herein. The processor 102 may be configured to acquire the user input from one or more user interfaces 104.

A user interface 104 may be any user interface that enables rendering (or output or display) of information, data or signals to a user of the apparatus 100. Alternatively or in addition, a user interface 104 may be any user interface that enables a user of the apparatus 100 to provide a user input, interact with and/or control the apparatus 100. For example, the user interface 104 may comprise one or more switches, one or more buttons, a keypad, a keyboard, a touch screen or an application (for example, on a tablet or smartphone), a display screen, a graphical user interface (GUI) or other visual rendering component, one or more speakers, one or more microphones or any other audio component, one or more lights, a component for providing tactile feedback (e.g. a vibration function), or any other user interface, or combination of user interfaces.

In some embodiments, the apparatus 100 may also comprise a memory 106 configured to store program code that can be executed by the processor 102 to perform the method described herein. Alternatively or in addition, one or more memories 106 may be external to (i.e. separate to or remote from) the apparatus 100. For example, one or more memories 106 may be part of another device. A memory 106 can be used to store models of anatomical structures, images of anatomical structures, information, data, signals and measurements acquired or made by the processor 102 of the apparatus 100 or from any interfaces, memories or devices that are external to the apparatus 100. For example, a memory 106 may be used to store one or more of the images in the sequence of images and/or the adjusted model of the anatomical structure. The processor 102 may be configured to control a memory 106 to store the adjusted model and/or the images from the sequence of images.

In some embodiments, the apparatus 100 may also comprise a communications interface (or circuitry) 108 for enabling the apparatus 100 to communicate with any interfaces, memories and devices that are internal or external to the apparatus 100. The communications interface 108 may communicate with any interfaces, memories and devices wirelessly or via a wired connection. For example, in an embodiment where one or more user interfaces 104 are external to the apparatus 100, the communications interface 108 may communicate with the one or more external user interfaces 104 wirelessly or via a wired connection. Similarly, in an embodiment where one or more memories 106 are external to the apparatus 100, the communications interface 108 may communicate with the one or more external memories 106 wirelessly or via a wired connection.

It will be appreciated that FIG. 1 only shows the components required to illustrate this aspect of the disclosure, and in a practical implementation the apparatus 100 may comprise additional components to those shown. For example, the apparatus 100 may comprise a battery or other power supply for powering the apparatus 100 or means for connecting the apparatus 100 to a mains power supply.

Figure 2:
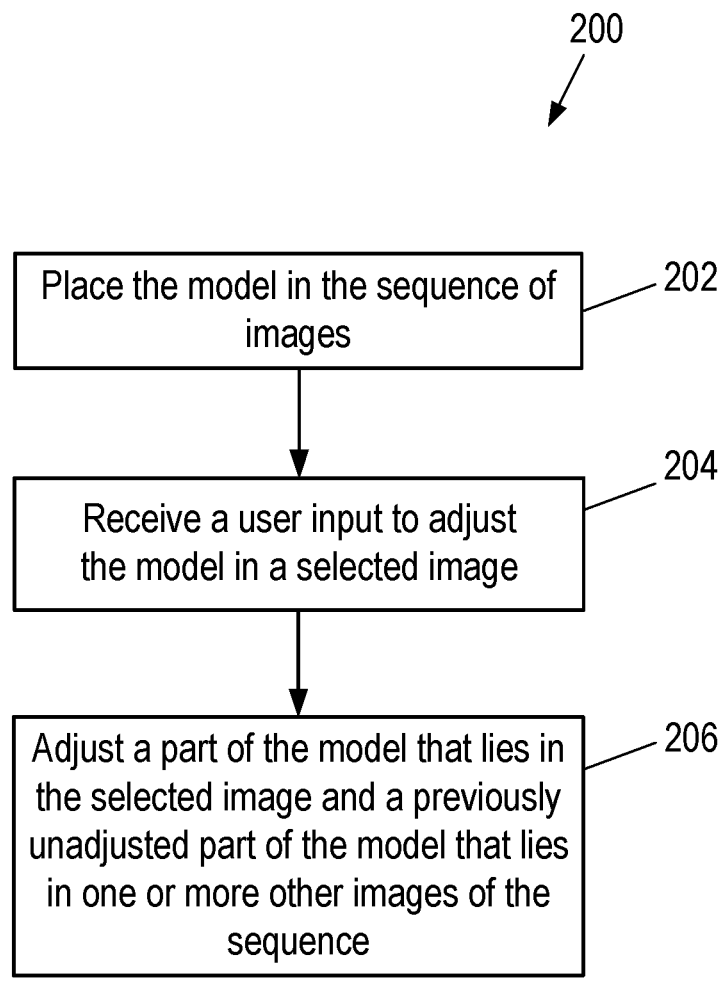
FIG. 2 illustrates a method for adjusting a model of an anatomical structure according to an embodiment.

FIG. 2 shows a block diagram illustrating a method 200 for adjusting a model of an anatomical structure in a sequence of images of the anatomical structure. The illustrated method 200 can generally be performed by or under the control of the processor 102 of the apparatus 100. The method 200 may, for example, be a computer-implemented method.

Briefly, the method 200 comprises placing the model of the anatomical structure with respect to the anatomical structure in the sequence of images (at block 202 of FIG. 2), receiving a user input to adjust (or modify) the model in a selected image of the sequence (at block 204 of FIG. 2), and adjusting (or modifying), based on the user input, a part of the model that lies in the selected image and a previously unadjusted (or unmodified) part of the model that lies in one or more other images of the sequence, whilst fixing (or freezing) in place a previously adjusted (or modified) part of the model that lies in other images of the sequence (at block 206 of FIG. 2).

As used herein, the terms 'previously adjusted' and 'previously unadjusted' refer to whether a part of the model has already been adjusted by a user, for example, based on one or more earlier user inputs received in the manner described with reference to block 204 of FIG. 2. More specifically, a previously adjusted part of the model is a part of the model that has previously been adjusted from a received user input directed to that part of the model and an unadjusted part of the model is a part of the model that has not previously been adjusted from a user input directed to that part of the model. It is noted that the term 'previously adjusted' thus does not necessarily include parts of the model that have been automatically adjusted due to propagation of an adjustment made by the user to another part of the model in another image.

In this way, changes made by the user to the model are only propagated to parts of the model lying in images of the sequence that have not already been adjusted by the user. Thus, parts of the model lying in images of the sequence that have been previously adjusted are fixed (or frozen) in place. This eliminates the need for the user to have to repeatedly check and re-adjust parts of the model that have already previously been adjusted and approved by the user. In this way, the workflow is simpler and more efficient, saving time for the user, and also produces more reliably adjusted models of anatomical structures since errors propagating through images in the sequence are avoided.

The anatomical structure referred to herein may be any anatomical structure. For example, the anatomical structure may be an organ, such as, for example, a heart, a lung or a pair of lungs, a brain, an intestine, a liver, a kidney, or any other anatomical structure, or any combination of anatomical structure. The anatomical structure can comprise one or more anatomical parts. For example, images of the heart can comprise a ventricle, an atrium, an aorta, or any other part of the heart, or any combination of parts of the heart.

The sequence of images of the anatomical structure referred to herein may, for example, comprise a sequence of medical images. The images may be acquired using any imaging modality. Examples of medical images include, but are not limited to computed tomography (CT) images (such as C-arm CT images, Spectral CT images, or Phase Contrast CT images), magnetic resonance (MR) images, X-ray images, ultrasound (US) images, fluoroscopy images, positron emission tomography (PET) images, single photon emission computed tomography (SPECT) images, nuclear medicine images, or any other medical images. In general, the images in the sequence of images can be of any image format (for example, a Digital Imaging and Communications in Medicine DICOM image format, or any other image format). For example, the image format may be any format suitable for allowing a model to be placed in the sequence of images.

In any of the embodiments described herein, the sequence of images can, for example, comprise a sequence of two-dimensional images, such as a time sequence of two-dimensional images. In these embodiments, each two-dimensional image in the sequence may show the anatomical structure at a subsequent point in time from the preceding two-dimensional image in the sequence. For example, in some embodiments, the sequence of images may comprise a sequence of two-dimensional images of a part of a heart, showing the heart over time in two-dimensions, at different stages of a heartbeat.

Alternatively, in any of the embodiments described herein, the sequence of images can, for example, comprise a sequence of two dimensional slices through a three-dimensional image. In these embodiments, each slice of the three-dimensional image in the sequence may show the anatomical structure at a subsequent two-dimensional spatial plane from the preceding slice of the three-dimensional image in the sequence. In some embodiments, for example, a three-dimensional image may be displayed to a user as a series of two-dimensional slices through the three-dimensional image volume. For example, where a series of two-dimensional slices (or scans) are taken to build up a three-dimensional volume (for example, in a computed tomography CT scan), the slices may be presented to the user in the sequence in which the image slices are taken. However, the sequence of two-dimensional slices through the three-dimensional volume does not necessarily have to align with the imaging direction. For example, in some embodiments, the two-dimensional slices through the three dimensional volume may be taken at any (arbitrary) angle with respect to the edges of the volume.

Alternatively, in any of the embodiments described herein, the sequence of images can, for example, comprise a sequence of three-dimensional images, such as a time sequence of three-dimensional images. In these embodiments, each three-dimensional image in the sequence may show the anatomical structure at a subsequent point in time from the preceding three-dimensional image in the sequence. For example, in some embodiments, the sequence of images may be a sequence of three-dimensional images of a part of a heart, showing the heart over time in three-dimensions, at different stages of a heartbeat.

Although examples have been provided for the type of images in the sequence and for the anatomical structure in the sequence of images, it will be understood that the apparatus and method described herein may also be used for adjusting a model of any other anatomical structure in any other type of image.

Turning now to the model of the anatomical structure, in any of the embodiments described herein, the model of the anatomical structure may be, for example, a geometric model representing a shape of an anatomical structure. The model may, for example, be a model used in a model-based segmentation of the anatomical structure in the sequence of images. Thus, in some embodiments, the model can be a segmentation model. The model can be a deformable model. In embodiments where the sequence of images comprises a sequence of two-dimensional images, the model may be a two-dimensional model. In embodiments where the sequence of images comprises a sequence of two dimensional slices through a three-dimensional image or a sequence of images a sequence of three-dimensional images, the model may be a three-dimensional model.

The model of the anatomical structure can comprise a plurality of segments. In some embodiments, for example, the model can comprise a mesh. In some embodiments, the mesh can be a polygon mesh. In these embodiments, the model can thus comprise a plurality of polygon segments. For example, the mesh may be a triangular mesh according to some embodiments. In these embodiments, the model can thus comprise a plurality of triangular segments. However, it will be understood that any other polygon mesh can be used for the model. In some embodiments, the plurality of segments (or the mesh) may be structured. For example, the plurality of segments may each be the same shape and optionally the same size. In other embodiments, the plurality of segments (or the mesh) may be unstructured. For example, one or more of the plurality of segments may be different shapes, one or more of the plurality of segments may be different sizes, or both. In some embodiments, the model (for example, the mesh) may comprise a plurality of control points. In these embodiments, each control point can define a point on a surface of the anatomical structure that is represented by the model.

Although examples have been provided for the type of model, a person skilled in the art will appreciate that other types of models may be used herein. For example, in some embodiments, the model may be a mask, such as a labelled mask, or any other type of model of which the person skilled in the art will be aware.

In embodiments where the sequence of images comprises a time sequence of two-dimensional images, each image in the sequence may show a two-dimensional representation of the same part of the anatomical structure at a different point in time. In these embodiments, the model of the anatomical structure may comprise a plurality of two-dimensional representations of the anatomical structure and there may be a representation for each of the two-dimensional images in the sequence. In some embodiments, the plurality of representations in the model may be linked to each other such that adjusting a part of the model in a first two-dimensional image of the sequence, adjusts an equivalent part of the model in another representation of the anatomical structure that is previously unadjusted and lies in another two-dimensional image of the sequence.

Similarly, in embodiments where the sequence of images comprises a sequence of three-dimensional images, each image in the sequence may show a three-dimensional representation of the same part of the anatomical structure at a different point in time. In these embodiments, the model of the anatomical structure may comprise a plurality of three-dimensional representations of the anatomical structure and there may be a representation for each of the three-dimensional images in the sequence. In some embodiments, the plurality of representations in the model may be linked to each other such that adjusting a part of the model in a first three-dimensional image of the sequence, adjusts an equivalent part of the model in another representation of the anatomical structure that is previously unadjusted and lies in another three-dimensional image of the sequence.

Returning back to FIG. 2, as mentioned earlier, at block 202 of FIG. 2, the model of the anatomical structure is placed (or positioned) with respect to the anatomical structure in the sequence of images. In some embodiments, placing the model with respect to the anatomical structure in the sequence of images at block 202 may comprise detecting the anatomical structure in the sequence of images to place the model at the location of the anatomical structure in the sequence of images. For example, where the anatomical structure is a heart, this can comprise detecting the heart, or a part of the heart (such as the mitral valve, or any other part of the heart), in the sequence of images. The anatomical structure may be detected in the sequence of images using any suitable feature extraction technique (such as the Generalized Hough Transformation GHT, or any other feature extraction technique).

Alternatively or in addition, in some embodiments, placing the model with respect to the anatomical structure in the sequence of images at block 202 of FIG. 2 may comprise segmenting the anatomical structure in the sequence of images. For example, the segmentation may comprise fitting the model to one or more parts of an anatomical structure, and/or one or more anatomical structures, in the sequence of images. This can be performed using any suitable segmentation technique (such as any model-based segmentation technique) and the person skilled in the art will be familiar with various segmentation methods that might be used.

Although not illustrated in FIG. 2, in some embodiments, the method 200 may further comprise rendering or displaying one or more images from the sequence of images on a user interface 104 (such as a display device) for presentation to the user. The one or more images from the sequence can be rendered or displayed with the model placed in the one or more images. For example, a representation of at least part the model may be rendered or displayed overlaying the one or more images.

In some embodiments, the images in the sequence can be displayed to the user in sequence (e.g. in a predetermined order) and thus the parts of the model that are previously adjusted or previously unadjusted depend on the ordering of the sequence, as will be described below.

At block 204 of FIG. 2, as mentioned earlier, a user input is received to adjust the model in a selected image of the sequence. In some embodiments, a user input to adjust the model in a selected image of the sequence may comprise receiving a user input indicating an adjustment to part of the model in the selected image. For example, the user may "drag and drop" part of the model (for example, a control point of the model) from one point in the selected image to another point in the selected image, using a user interface 104 (for example, a mouse, a touch screen, or any other user interface, such as any of those described earlier). The user input may provide an indication of a path or a vector through which to move the part of the model in the selected image.

Generally, the selected image referred to herein is the image that is currently being viewed, assessed and/or in which a part of the model is being adjusted by a user. In some embodiments, the selected image can be any image in the sequence of images that is selected by the user. For example, in some embodiments, the user may select in which images in the sequence to adjust a part of the model of the anatomical structure. In some of these embodiments, the user may also select the order of images in the sequence in which to adjust a part of the model of the anatomical structure (and, as such, the user may choose to view the images of the sequence in any order). The user may select an image via a user interface 104. The processor 102 may receive an indication of the selection from the user interface 104.

In other embodiments, the selected image can be the current image in the sequence that is displayed to the user for the user to adjust a part of the model of the anatomical structure in the image. In some embodiments, each image may be displayed to the user in a predefined order for the user to adjust a part of the model of the anatomical structure in those images. For example, the predefined order may be a predefined time order, where the images in the sequence are displayed to the user in a chronological order or in a reverse chronological order.

In some embodiments where the sequence of images comprises a sequence of two-dimensional slices through a three-dimensional image volume, the predefined order may be a sequential order through the three-dimensional image volume, where the two-dimensional slices in the sequence are displayed to the user in the sequential order in which they appear in the three-dimensional image volume. For example, the two-dimensional slices may be displayed to the user in a predefined order that starts, for example, from one edge of the three-dimensional image volume and ends, for example, at an opposite edge of the three-dimensional image volume.

In some examples, the sequential order of two-dimensional slices through the three-dimensional image volume may be a sequential order of two-dimensional slices that are perpendicular to an axis associated with an anatomical feature of the anatomical structure in the three-dimensional image. For example, in some embodiments where the anatomical structure is a heart, the axis may be defined as an axis that runs through the left ventricle from the center of the mitral valve plane to the apex in the three-dimensional image. In this example, the sequence of images may then be displayed in an order to the user, either an order from the mitral valve plane to the apex or, conversely, an order from the apex to the mitral valve plane. In this way, the sequence of images is displayed to the user in a meaningful or intuitive way. In another example, instead of moving sequentially through a whole three-dimensional image volume, a long axis two-dimensional slice may be displayed initially and this may be followed by the display of a specific stack of short axis two-dimensional slices.

Although examples have been provided for an order in which the images of the sequence may be displayed to the user, the person skilled in the art will appreciate that other display orders are also possible.

Returning back to FIG. 2, at block 206, as mentioned earlier, a part of the model that lies in the selected image is adjusted based on the user input that is received and a previously unadjusted part of the model that lies in one or more other images of the sequence is adjusted based on the user input, whilst a previously adjusted part of the model that lies in other images of the sequence is fixed in place.

In some embodiments, adjusting, based on the user input, may comprise adjusting a part of the model that lies in the selected image and that is indicated by the user in the user input. For example, the user input may indicate movement of a part of the model that lies in the selected image to a new (or adjusted) position, where the new position is also indicated by the user. In this way, the position of a part of the model that lies in the selected image can be adjusted (for example, corrected), according to instructions provided by the user input.

In embodiments where the model of the anatomical structure comprises a mesh, which itself comprises a plurality of segments, the method may further comprise determining which of the plurality of segments lie in (or belong to) the selected image in the sequence and adjusting, based on the user input, one or more of the segments that are determined to lie in the selected image in the sequence. It may be determined, for example, that a segment of the model lies in (or belongs to) the selected image if more than a predefined percent (for example, 50 percent) of that segment lies in the selected image. In some embodiments, the one or more adjusted segments lying in the selected image may comprise at least one segment of the mesh to which the received user input relates and one or more adjacent segments.

In some embodiments, adjusting, based on the user input, a previously unadjusted part of the model that lies in one or more other images of the sequence may comprise propagating an adjustment indicated by the user input for a part of the model that lies in the selected image to one or more previously unadjusted parts of the model that lie in one or more other images of the sequence. For example, if it can be inferred from the adjustment to the part of the model in the selected image that one or more other parts of the model are to be adjusted, based on the user input, then the one or more other parts of the model are adjusted in the images in which those parts of the model lie, provided that those parts of the model have not previously been adjusted by the user. It may, for example, be inferred from the adjustment to the part of the model in the selected image that one or more other parts of the model are to be adjusted where the one or more other parts of the model are linked (for example, functionally linked and/or geometrically linked) to the part of the model in the selected image.

In some embodiments, adjusting, based on the user input, a previously unadjusted part of the model that lies in one or more other images of the sequence may comprise propagating an adjustment indicated by the user input for a part of the model that lies in the selected image to one or more previously unchecked parts of the model (e.g. parts of the model that have not yet been looked at by the user) that lie in one or more other images of the sequence. In this way, if it is identified that no adjustments have been made by the user to a part of the model that lies in a particular image that has been checked by the user, then the part of the model that lies in this particular image is effectively fixed (or frozen) in place. Thus in these embodiments, any subsequent adjustments made, based on a user input, to a part of the model that lies in a selected image are not propagated to previously checked parts of the model that lie in one or more other images of the sequence. In this way, the user can be certain that any parts of the model that have been previously checked (even if they have not been adjusted) are fixed in place and thus do not need to be checked again.

In some embodiments, a previously unadjusted part of the model that lies in one or more other images of the sequence may be adjusted by using an interpolation to adjust the previously unadjusted part of the model that lies in the one or more other images of the sequence, based on the adjustment to the part of the model that lies in the selected image. For example, one or more previously unadjusted parts of the model may also be adjusted in order to ensure one or more parts of the model have a smooth profile and/or in order to prevent discontinuities being introduced into the model.

The propagation of an adjustment made to a particular part of the model that lies in the selected image of the sequence to other previously unadjusted parts of the model that lie in one or more other images of the sequence can be achieved in a variety of ways. In some embodiments, for example, the adjustment may be propagated to one or more other images in which a previously unadjusted part of the model lies that are located within a certain radius of the selected image (for example, within a certain number of images preceding and/or subsequent to, the selected image in the sequence). For example, in some embodiments, an adjustment may only be propagated to images that are immediate neighboring images of the selected image in the sequence of images, or an adjustment may be propagated to a predetermined number x of the neighboring images in the sequence, where x is an integer value. In some embodiments, the adjustment may be propagated to images preceding and/or subsequent to the selected image in the sequence that were taken (e.g. recorded or scanned) within a predetermined time interval of the selected image.

In some embodiments, the one or more other images of the sequence (in which a previously unadjusted part of the model is adjusted) can be selected based on a property of the anatomical structure. In some embodiments, the property may be a functional property of the anatomical structure, such as the manner in which the anatomical property changes over time. For example, in embodiments where the anatomical structure is the heart, the property may be the heart rate. In an example embodiment, the sequence of images of an anatomical structure comprises a time sequence of two-dimensional images of a heart, where the heart beats at a rate of 60 beats per-minute. The heart in this example embodiment undergoes a full cardiac cycle each second. As such, any adjustments that are made to a part of the model of the heart in a selected image in the time-sequence of two-dimensional images are thus not propagated indefinitely through the time sequence of two-dimensional images, as the adjustments only apply to the particular point of the cardiac cycle that is shown in the selected image. In such embodiments, adjustments may be propagated to other images in the sequence of images corresponding to the same point of the cardiac cycle as the selected image.

In some embodiments, a size of an adjustment made by the user to a part of the model in the selected image may be weighted before the adjustment is also made to a previously unadjusted part of the model that lies in one or more other images. For example, the weighting applied to the adjustment may reduce the extent of the adjustment to the part of the model that lies in the one or more other images. In some embodiments, for example, the weighting applied to an adjustment may be based on the distance of each of the one or more other images from the selected image in the sequence such that the greater the distance between the selected image and the other image, the greater the reduction in the extent of the adjustment to the part of the model that lies in the other image. In some embodiments, the weighting applied to an adjustment may be proportional to the number of images in the sequence that are located between the selected image and the other image in which the previously unadjusted portion of the model lies. For example, the adjustment may be reduced exponentially in relation to the distance between the selected image and the other image.

In an embodiment where the anatomical structure is a heart, for example, the weighting may be proportional to (or may reflect) the phase of the cardiac cycle. Thus, if the heart is expected to contract by, for example, 30 percent between the selected image and the next image in the sequence, then the adjustment may be reduced by the same percentage. This may be used to ensure that an adjustment made to an image taken at a point in time corresponding to systole (e.g. contraction) of the heart is not applied to parts of the model in an image corresponding to diastole (e.g. relaxation) of the heart.

In some embodiments, as noted previously, a user can be permitted to view images of the sequence in any order and thus the user may select and adjust a part of the model in any image of the sequence. Considering an example of a sequence of two-dimensional slices through a three-dimensional image, if the user were to select two-dimensional slice number 13 of the sequence as an image in which to adjust a part of the model and the parts of the model lying in neighboring two-dimensional slices have not previously been adjusted, then the adjustment is propagated to the neighboring slices in three-dimensions in both directions (for example, to slice number 13−− and slice number 13++). If, in the next adjustment, the user selects a part of the model lying in two-dimensional slice number 10 to adjust, the adjustment to the part of the model lying in slice number 10 will not be propagated to slice number 13 because slice number 13 was previously adjusted by the user in the earlier operation. The adjustment to the part of the model lying in slice number 10 will, however, be propagated to slice numbers 1-10, 11, 12 and 14++ because these were previously unadjusted by the user.

In some embodiments, the previously unadjusted part of the model may lie in one or more images that are subsequent to the selected image in the sequence and the previously adjusted part of the model may lie in images that precede the selected image in the sequence. For example, in some embodiments where the sequence of images are displayed to the user in a predefined order (as described earlier), adjusting at block 206 of FIG. 2 can comprise adjusting, based on the user input, a part of the model that lies in the selected image and a part of the model that lies in one or more images that are subsequent to the selected image according to the predefined order, whilst fixing in place a part of the model that lies in images that precede the selected image according to the predefined order. Thus, in some embodiments, adjustments are propagated in one direction through the sequence of images to images in the sequence in which the model has not yet been adjusted by the user, while adjustments are not propagated to preceding images in the sequence in which a part of the model has already been adjusted by the user. In such embodiments, therefore, the previously adjusted part of the model lies in images that precede the selected image in the sequence and the previously unadjusted part of the model lies in one or more images that are subsequent to the selected image in the sequence.

In this way, the model adjustment only affects the parts of the model that belong to the current image in which a part of the model is being adjusted and to those images in which a part of the model has not yet been adjusted (for example, those images in which a part of the model may still need adjustment in the future). The parts of the model that have already been adjusted remain unchanged. As a result, the user can be sure that current adjustments do not introduce errors in already adjusted parts of the model and the user does not have to check and re-adjust parts of the model in previous images again. Thus, the workflow of the user is made more efficient.

In any of the embodiments described herein, once the adjustments have been made to the selected image, in some embodiments, the method 200 further comprises fixing in place the adjusted part of the model that lies in the selected image for subsequent adjustments. The method 200 may then be repeated on one or more subsequent images, for example, the method 200 may further comprise receiving at least one further user input to adjust the model in at least one further image in the sequence and adjusting, based on the at least one further user input, a part of the model that lies in the at least one further image, whilst fixing in place a previously adjusted part of the model that lies in other images of the sequence.

In this way, once the user has adjusted a part of the model in the image, that part of the model is effectively "frozen". Subsequent adjustments to other parts of the model in the image may be propagated through to other images in the sequence, but will not affect parts of the model that have already been adjusted (and, for example, checked) by the user. This makes the adjustment (and, for example, checking) process more efficient by ensuring that the user does not have to re-adjust parts of the model that have already been adjusted.

Figure 3:
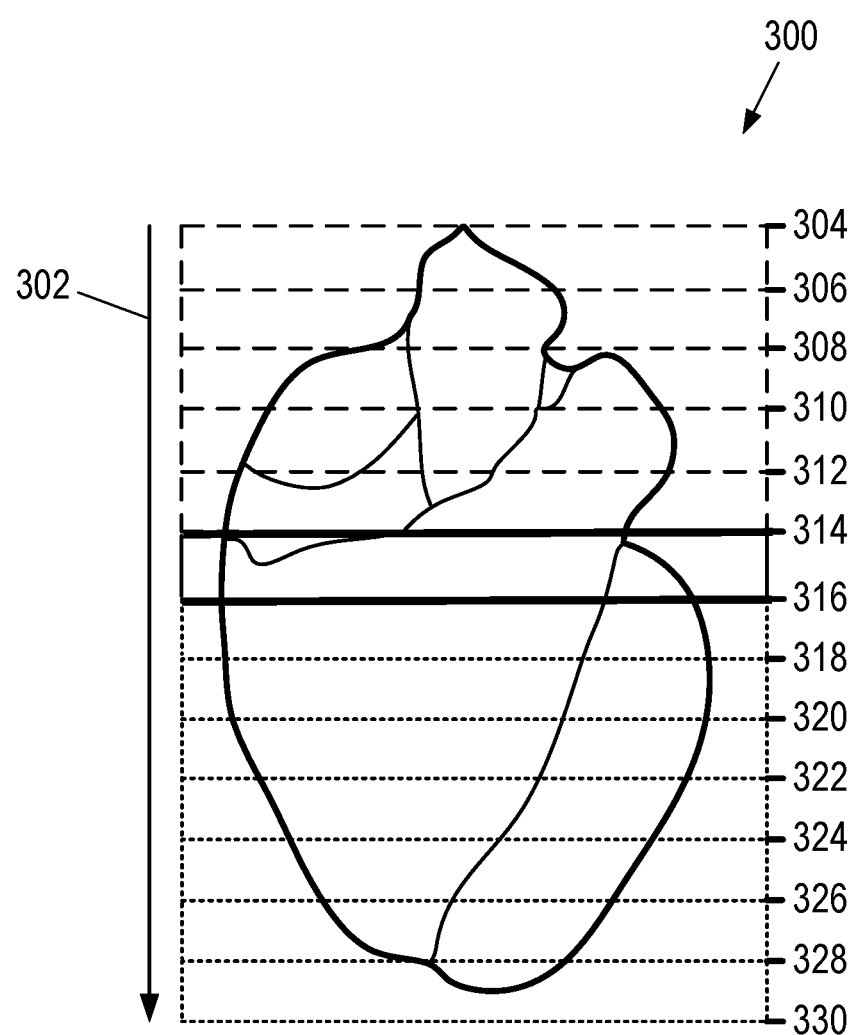
FIG. 3 illustrates an example embodiment of a method of adjusting a model of an anatomical structure in use.

FIG. 3 illustrates an example embodiment of a method of adjusting a model of an anatomical structure in use according to an embodiment. More specifically, the example embodiment illustrated in FIG. 3 shows a three-dimensional short axis cine magnetic resonance MR image of a heart. The heart has been segmented using a three-dimensional model. Although not illustrated in FIG. 3, the three-dimensional model comprises a mesh, which itself comprises a plurality of segments (for example, a plurality of triangular segments).

The three-dimensional image comprises a sequence of two-dimensional slices. The two-dimensional slices 304 to 328 are displayed to the user in an order, starting from the top of the three-dimensional image in a plane that is perpendicular to the plane of FIG. 3, along the imaging direction of the arrow 302. The imaging direction shown in FIG. 3 is from the mitral valve plane to the apex. In this example embodiment, the two-dimensional slices correspond to the imaging slices of the MR imaging technique and the two-dimensional slices in the sequence are displayed to the user in the imaging direction, such that the two-dimensional slice that was acquired first during imaging is the first two-dimensional slice to be displayed to the user and the two-dimensional slice that was acquired last during imaging is the last two-dimensional slice to be displayed to the user.

As mentioned earlier, although not illustrated in FIG. 3, the three-dimensional model comprises a mesh, which itself comprises a plurality of segments. The segments of the mesh overlay the anatomical structure in the sequence of two-dimensional slices and the segments of the mesh can be adjusted by the user to adjust parts of the model. In the example embodiment of FIG. 3, the two-dimensional slice 314 is the selected slice, which is the current slice in which a part of the model is being adjusted by the user. The two-dimensional slices 304, 306, 308, 310, and 312 are slices in which a part of the model has previously been adjusted by the user and are therefore fixed in place. In some embodiments, the slices 304, 306, 308, 310, and 312 may be marked as "frozen".

The two-dimensional slices 318 to 328 are slices in which a part of the model is previously unadjusted by the user. In practice, in the example embodiment of FIG. 3, for each adjustment that is made by the user to the part of the model (or, more specifically, to the mesh of the model) that lies in the selected slice 314, an adjustment is also made to a part of the model lying in one or more previously unadjusted parts of the model (or, more specifically, one or more parts of the mesh of the model) lying in one or more of the slices 318 to 328. The user may adjust the part of the model that lies in the selected slice 314 by adjusting one or more control points of the model. Once the user has finished adjusting the part of the model that lies in the selected slice 314, the part of the model belonging to slice 314 is classed as a previously adjusted part of the model, which is then fixed in place to prevent future adjustments to that part of the model. Then, in this example embodiment, the next slice 316 in the sequence of two-dimensional slices is displayed for adjustment by the user in the same way as described earlier for slice 314. This process can be repeated for each image slice 318 to 328 in which a previously unadjusted part of the model lies in order. In this way, the model of the anatomical structure is adjusted in the sequence of two-dimensional slices according to the method described herein.

In any of the embodiments described herein, the previously adjusted parts of the model that are fixed in place may be color-coded in a different color to the previously unadjusted parts of the model. In some embodiments, the part of the model that is being adjusted in the selected image may be color-coded in a different color to the previously unadjusted parts of the model and/or the previously adjusted parts of the model. In embodiments where the model comprises a mesh, which itself comprises a plurality of segments, the segments of the mesh that correspond to a part of the model that is fixed in place may be color-coded in a different color to segments of the mesh that correspond to a part of the model that is previously unadjusted to indicate to the user that those parts of the model are fixed in place. If the model is displayed at a user interface 104 (for example, in a viewer of a user interface 104), the user is provided with immediate knowledge of which parts of the model can still be adjusted.

There is therefore provided an improved method and apparatus for adjusting a model of an anatomical structure in a sequence of images of the anatomical structure.

There is also provided a computer program product comprising a computer readable medium, the computer readable medium having computer readable code embodied therein, the computer readable code being configured such that, on execution by a suitable computer or processor, the computer or processor is caused to perform the method or methods described herein. Thus, it will be appreciated that the disclosure also applies to computer programs, particularly computer programs on or in a carrier, adapted to put embodiments into practice. The program may be in the form of a source code, an object code, a code intermediate source and an object code such as in a partially compiled form, or in any other form suitable for use in the implementation of the method according to the embodiments described herein.

It will also be appreciated that such a program may have many different architectural designs. For example, a program code implementing the functionality of the method or system may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other.

An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for adjusting a model of an anatomical structure in a sequence of images of the anatomical structure, the method comprising:
    placing the model with respect to the anatomical structure in the sequence of images;
    receiving a user input to adjust the model in a selected image of the sequence; and
    adjusting, based on the user input, a part of the model that lies in the selected image and a previously unadjusted part of the model that lies in one or more other images of the sequence, whilst fixing in place a previously adjusted part of the model that lies in other images of the sequence.

2. A method as claimed in claim 1, wherein the previously unadjusted part of the model lies in one or more images that are subsequent to the selected image in the sequence and the previously adjusted part of the model lies in images that precede the selected image in the sequence.

3. A method as claimed in claim 1, the method further comprising:
    fixing in place the adjusted part of the model that lies in the selected image for subsequent adjustments.

4. A method as claimed in claim 1, wherein adjusting a previously unadjusted part of the model that lies in the one or more other images of the sequence comprises:
    using an interpolation to adjust the previously unadjusted part of the model that lies in the one or more other images of the sequence, based on the adjustment to the part of the model that lies in the selected image.

5. A method as claimed in claim 1, the method further comprising:
    receiving at least one further user input to adjust the model in at least one further image in the sequence; and
    adjusting, based on the at least one further user input, a part of the model that lies in the at least one further image, whilst fixing in place a previously adjusted part of the model that lies in other images of the sequence.

6. A method as claimed in claim 1, wherein the one or more other images of the sequence in which a previously unadjusted part of the model is adjusted are selected based on a property of the anatomical structure.

7. A method as claimed in claim 1, wherein the one or more other images of the sequence in which a previously unadjusted part of the model is adjusted lie within a predetermined radius of the selected image.

8. A method as claimed in claim 1, wherein the sequence of images comprises:
   a time sequence of two-dimensional images, wherein each two-dimensional image in the sequence shows the anatomical structure at a subsequent point in time from the preceding two-dimensional image in the sequence.

9. A method as claimed in claim 1, wherein the sequence of images comprises:
   a sequence of two-dimensional slices through a three-dimensional image, wherein each slice of the three-dimensional image in the sequence shows the anatomical structure at a subsequent two-dimensional spatial plane from the preceding slice of the three-dimensional image in the sequence.

10. A method as claimed in claim 1, wherein the sequence of images comprises:
    a time sequence of three-dimensional images, wherein each three-dimensional image in the sequence shows the anatomical structure at a subsequent point in time from the preceding three-dimensional image in the sequence.

11. A method as claimed in claim 1, wherein the model of the anatomical structure comprises a mesh comprising a plurality of segments and wherein the method further comprises:
    determining which of the plurality of segments lie in the selected image in the sequence; and
    adjusting, based on the user input, one or more of the segments that are determined to lie in the selected image in the sequence.

12. A method as claimed in claim 10, wherein the one or more adjusted segments lying in the selected image comprise at least one segment of the mesh to which the received user input relates and one or more adjacent segments.

13. A computer program product comprising a non-transitory computer readable medium, the non-transitory computer readable medium having computer readable code embodied therein, the computer readable code being configured such that, on execution by a suitable computer or processor, the computer or processor is caused to perform the method of claim 1.

14. An apparatus for adjusting a model of an anatomical structure in a sequence of images of the anatomical structure, the apparatus comprising:
    a processor configured to:
    place the model with respect to the anatomical structure in the sequence of images;
    receive a user input to adjust the model in a selected image of the sequence; and
    adjust, based on the user input, a part of the model that lies in the selected image and a previously unadjusted part of the model that lies in one or more other images of the sequence, whilst fixing in place a previously adjusted part of the model that lies in other images of the sequence.

15. An apparatus as claimed in claim 14, wherein the processor is configured to:
    control a user interface to render the adjusted model of the anatomical structure; and/or
    control a memory to store the adjusted model of the anatomical structure.

* * * * *